(12) United States Patent
Fujisawa et al.

(10) Patent No.: US 8,813,554 B2
(45) Date of Patent: Aug. 26, 2014

(54) METHODS AND APPARATUS TO ESTIMATE FLUID COMPONENT VOLUMES

(75) Inventors: Go Fujisawa, Sagamihara (JP); Andrew J. Carnegie, Perth (AU); Jack H. Harfoushian, Perth (AU); Saifon Daungkaew Sirimongkolkitti, Nakhonsithammarat (TH); Oliver C. Mullins, Ridgefield, CT (US)

(73) Assignee: Schlumberger Technology Corporation, Sugar Land, TX (US)

( * ) Notice: Subject to any disclaimer, the term of this patent is extended or adjusted under 35 U.S.C. 154(b) by 468 days.

(21) Appl. No.: 13/149,901

(22) Filed: Jun. 1, 2011

(65) Prior Publication Data

US 2012/0304757 A1 Dec. 6, 2012

(51) Int. Cl.
E21B 49/08 (2006.01)

(52) U.S. Cl.
CPC .................................. *E21B 49/081* (2013.01)
USPC ..................................................... 73/152.27

(58) Field of Classification Search
CPC ................................................ E21B 49/081
USPC .......... 175/59; 166/264, 100, 107; 73/152.23, 73/152.27, 153.28
See application file for complete search history.

(56) References Cited

U.S. PATENT DOCUMENTS

| | | | |
|---|---|---|---|
| 6,230,557 B1 | 5/2001 | Ciglenec | 73/152.01 |
| 6,476,384 B1 | 11/2002 | Mullins et al. | 250/269.1 |
| 6,768,105 B2 | 7/2004 | Mullins et al. | 250/269.1 |
| 6,986,282 B2 | 1/2006 | Ciglenec | 73/152.51 |
| 7,114,562 B2 | 10/2006 | Fisseler et al. | 166/250.02 |
| 2004/0216874 A1* | 11/2004 | Grant et al. | 166/264 |

* cited by examiner

*Primary Examiner* — John Fitzgerald
(74) *Attorney, Agent, or Firm* — Daryl R. Wright; Jody DeStefanis

(57) ABSTRACT

Methods of and apparatus to estimate one or more volumes of one or more components of a fluid in a sample chamber of a downhole tool are described. An example method includes obtaining a sample chamber volume measurement, a flowline volume measurement and a supplemental volume measurement. The example method includes drawing the fluid into the sample chamber until the sample chamber is substantially full and measuring a characteristic of the fluid in the sample chamber at a first time to obtain a first characteristic measurement. The example method also includes adding a supplemental volume corresponding to the supplemental volume measurement to over-pressurize the sample chamber after measuring the characteristic at the first time and measuring the characteristic of the fluid in the sample chamber at a second time to obtain a second characteristic measurement. The second time is after the sample chamber is over-pressurized. In addition, the example method includes calculating a first volume of a first component of the one or more components of the fluid based on the first characteristic measurement, the second characteristic measurement, the sample chamber volume measurement, the flowline volume measurement and the supplemental volume measurement.

30 Claims, 9 Drawing Sheets

METHODS AND APPARATUS TO ESTIMATE FLUID COMPONENT VOLUMES

FIELD OF THE DISCLOSURE

This disclosure relates generally to oil and gas production and, more particularly, to methods and apparatus to estimate fluid component volumes.

BACKGROUND OF THE DISCLOSURE

Over the past several decades, highly sophisticated techniques have been developed for identifying and producing hydrocarbons, commonly referred to as oil and gas, from subsurface formations. These techniques facilitate the discovery, assessment, and production of hydrocarbons from subsurface formations.

Downhole fluid analysis (DFA) is an important and efficient investigative technique typically used to ascertain the characteristics and nature of geological formations having hydrocarbon deposits. DFA is used in oilfield exploration and development for determining petrophysical, mineralogical and fluid properties of hydrocarbon reservoirs. In particular, DFA may be used to analyze the properties and phase behavior of downhole fluids which, in turn, may be used to characterize hydrocarbon reservoirs.

Typically, a complex mixture of fluids, such as oil, gas, and water, is found downhole in reservoir formations. The downhole fluids, which are also referred to as formation fluids, have characteristics or properties including pressure, live fluid color, dead-crude density, gas-oil ratio (GOR), among other fluid properties, that may be used to characterize hydrocarbon reservoirs.

To evaluate and test underground formations surrounding a borehole, it is often desirable to obtain samples of formation fluids for purposes of characterizing the fluids. Tools have been developed which allow samples to be taken from a formation in a logging run or during drilling. The Reservoir Formation Tester (RFT) and Modular Formation Dynamics Tester (MDT) tools provided by Schlumberger are examples of sampling tools for extracting samples of formation fluids for analysis at the surface.

Recent developments in DFA include techniques for characterizing formation fluids downhole in a wellbore or borehole rather than or in addition to analysis at the surface. Specifically, Schlumberger's MDT tool may include one or more fluid analysis modules, such as the Composition Fluid Analyzer (CFA) and Live Fluid Analyzer (LFA), to analyze downhole fluids sampled by the tool while the fluids are still downhole.

In DFA modules of the type mentioned above, formation fluids that are to be analyzed downhole flow past sensor modules, such as spectrometer modules, which analyze the fluids by near-infrared (NIR) absorption spectroscopy, for example. Co-owned U.S. Pat. Nos. 6,476,384 and 6,768,105 are examples of patents relating to the foregoing techniques, the contents of these patents are incorporated herein by reference in their entireties. Formation fluids also may be captured in sample chambers associated with the DFA modules, having sensors, such as pressure/temperature gauges, embedded therein for measuring fluid properties of the captured formation fluids.

SUMMARY

Example methods of estimating one or more volumes of one or more components of a fluid in a sample chamber of a downhole tool are described. An example method includes obtaining a sample chamber volume measurement, a flowline volume measurement and a supplemental volume measurement. The example method includes drawing the fluid into the sample chamber until the sample chamber is substantially full and measuring a characteristic of the fluid in the sample chamber at a first time to obtain a first characteristic measurement. The example method also includes adding a supplemental volume corresponding to the supplemental volume measurement to over-pressurize the sample chamber after measuring the characteristic at the first time and measuring the characteristic of the fluid in the sample chamber at a second time to obtain a second characteristic measurement. The second time is after the sample chamber is over-pressurized. In addition, the example method includes calculating a first volume of a first component of the one or more components of the fluid based on the first characteristic measurement, the second characteristic measurement, the sample chamber volume measurement, the flowline volume measurement and the supplemental volume measurement.

Example tangible machine readable mediums having instructions stored thereon which, when executed, cause a machine to estimate one or more volumes of one or more components of a fluid in a sample chamber of a downhole tool are also described. One example machine readable medium having instruction stored thereon which, when executed, causes the machine to obtain a sample chamber volume measurement, a flowline volume measurement and a supplemental volume measurement. The machine is also caused to draw the fluid into the sample chamber until the chamber is substantially full and measure a characteristic of the fluid in the sample chamber at a first time to obtain a first characteristic measurement. The machine is also caused to add a supplemental volume corresponding to the supplemental volume measurement to over-pressurize the sample chamber after the measuring of the characteristic at the first time and measure the characteristic of the fluid in the sample chamber at a second time to obtain a second characteristic measurement. The second time is after the sample chamber is over-pressurized. In addition, the machine readable instructions on the medium readable medium, when executed, cause the machine to calculate a first volume of a first component of the one or more components of the fluid based on the first characteristic measurement, the second characteristic measurement, the sample chamber volume measurement, the flowline volume measurement and the supplemental volume measurement.

Furthermore, example downhole tools are described. An example downhole tool includes a sample chamber having a sample chamber volume, a flowline coupled to the sample chamber and having a flowline volume and a pump to pump a fluid into the sample chamber through the flowline. The example tool also includes a sensor to measure a characteristic of the fluid in the sample chamber when the sample chamber is substantially full at a first time to obtain a first characteristic measurement and to measure the characteristic of the fluid in the sample chamber at a second time to obtain a second characteristic measurement. The first time is before the pump over-pressurizes the sample chamber, and the second time is after the pump pumps a supplemental volume into the sample chamber to over-pressurize the sample chamber. In addition, the example downhole tool includes a calculator to determine a first volume of a first component of the one or more components of the fluid based on the first characteristic measurement, the second characteristic measurement, the sample chamber volume, the flowline volume and the supplemental volume.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1A:
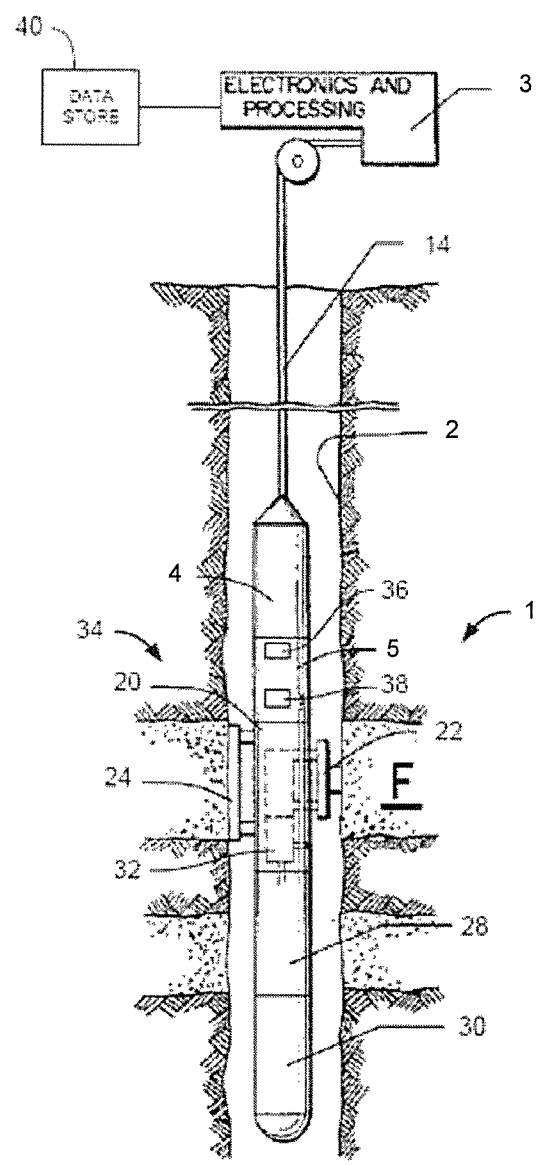
FIG. 1A illustrates an example wireline tool.

It is to be understood that the following disclosure provides many different embodiments or examples for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various examples and/or configurations discussed. Moreover, the formation of a first feature over or on a second feature in the description that follows may include examples in which the first and second features are formed in direct contact, and may also include examples in which additional features may be formed interposing the first and second features, such that the first and second features may not be in direct contact.

It is valuable to know the volume fractions or percentages of oil, gas and water captured in a sample bottle or sample chamber during the testing of a subsurface formation. The fluid types may be monitored by, for example, Schlumberger's MDT modular formation dynamics tester tool including, for example, downhole fluid analysis (DFA) modules such as the live fluid analyzer (LFA) module, the composition fluid analyzer (CFA) module, the LFA-pH module and the InSitu Fluid Analyzer (IFA) tools provided by Schlumberger. The volume fractions or percentages of the component(s) of the fluid sampled by the tools can be estimated by adding up the volume of each phase of material observed by these tools. For example, if the DFA module(s) measure 250 cc of gas, 150 cc of oil and 100 cc of water passing in the flowline during the capturing of a 500 cc sample, the volume estimation will be 50% gas, 30% oil and 20% water captured in the sample chamber.

However, the above-noted direct calculation becomes invalid in three situations. First, if the pressure and to some extent the temperature, is different between the measurement point of the DFA module and the sample chamber, the volume fractions will be different between these two points due to differences in compressibility of the fluid components and/or the phases of those component. For example, if the pressure inside the sample chamber is higher than the flowline pressure at the point of DFA module measurement, the volume fraction occupied by gas (e.g., hydrocarbon gas) in the sample chamber will be less due to the higher compressibility of the gas compared to the liquid oil and the liquid water.

Second, the different component and/or phases have different velocities, which lead to the different components and/or phases having different cuts (fraction of the total flow rate of a fluid attributable to the phase) and holdups (fraction of total fluid in an interval of pipe attributable to the phase). Thus, the volume of each component and/or phase captured in the sample chamber may differ from the volume observed by the DFA module at the measurement point.

Third, in most situations the gas (e.g., hydrocarbon gas) may contain vapor (e.g., oil vapor and/or water vapor) and the liquid oil and/or the liquid water may contain some dissolved gas. The amount of admissive vapor in the gas and dissolved gas in the liquids depends on the pressure, temperature and fluid compositions. If the fluid pressure and temperature are different between the measurement point and the sample chamber, some fraction of molecules will move from one phase to another to reach a new equilibrium. In this case, the definition of the gas and the oil and/or water will be different between the point of measurement, i.e., at the DFA module, and the point of the sample chamber.

Further, one of the conditions in which this direct estimation gives a large error is for a fluid system containing gas and liquid phase at low pressure. For example, consider a situation that dry gas and water are produced at reservoir pressure of 1000 psi and pumped by an MDT pump-out module to compress fluid up to 4000 psi for the purpose of capturing the fluid in a sample chamber. Under such pressure, the dry gas volume will shrink to about one quarter of its original volume, whereas the water volume will remain almost unchanged. In addition, due to velocity differences magnified by presence of the MDT pump module, there will be a large difference between volume fractions observed by the DFA module and those observed in the fluid captured in the sample chamber.

The examples described herein provide processes for accurately estimating the fluid component volumes and/or percentages. In particular, the examples described herein provide accurate estimates of the fluid component volumes even where there are different phase velocities and in situations involving highly compressible low pressure gas.

In one example method described herein, fluid characteristics are measured and equations of state (e.g., pressure and temperature) are solved. In one example, the fluid system includes a highly compressible gas (e.g. a material in a gaseous state such as 100% methane gas) and at least one almost non-compressible liquid (e.g. a material in a liquid state such as liquid water). Pressure is sufficiently low for the target fluid system to ignore the effect of mass transfer from one phase to another. In other words, solubility of a gas into non-compressible liquid and vaporization of liquid into compressible gas can be approximated as constant without causing a significant error to the final result. In the examples described herein, liquid water may be referred as non-compressive fluid or phase, which is an approximation of the state of the water and a description of the water relative to gas phases, which have higher magnitudes of compressibility—by several orders. Likewise, liquid oil may be approximated as a non-compressive phase as opposed to a more compressive gas phase.

In an example, the compressible gas phase or gas is mostly methane or another gas composition, which can be reliably identified by the DFA module such as the CFA module or the IFA tool in real time, so that a known equation of state can predict the gas phase volume at given pressure and temperature with a reasonable accuracy. Also, the non-compressible liquid phase or liquid is water and/or liquid hydrocarbon of another composition such as synthetic oil-based mud. For a given pressure range (e.g. 1000~4000 psi), the volume change of the gas and/or liquid can be negligible or calculated by a known equation of state with a reasonable accuracy.

In this example, as described in greater detail below, the total volume of the high pressure side of a pumpout module is calculated, i.e., the total volume of a sample chamber and the flowline volume between sample chamber and pumpout. In addition, a supplemental volume is determined. The supplemental volume is an amount of extra volume that is pumped to over-pressurize the sample chamber after the sample chamber is substantially filled. In some examples, the supplemental volume is equal to the volume of one pumpout stroke, i.e., a piston stroke which, for the standard pumpout module, for example, may be less than 0.5 liter. In other examples, the supplemental volume is a fraction or a multiple of the piston stroke volume. At the end of the sample chamber filling, i.e., when the sample chamber is substantially filled, the example method, as noted above, includes pumping the supplemental volume to over-pressurize the sample chamber before the sample chamber is closed or isolated. The fluid pressure and temperature are measured above the pumpout at the beginning of or before ($t_1$) and end of or after ($t_2$) the over-pressurizing supplemental volume being pumped. The two temperature and pressure readings and the known volumes are used, in accordance with the equations presented below, for example, to determine the volume of the components of the fluid, i.e., the volumes of the non-compressible liquid (e.g., water) and the compressible gas in the sample chamber.

In another example, gas density information is used to determine the fluid component volumes. In one example, the fluid system includes a highly compressible gas phase (e.g. 100% methane gas) and at least one substantially non-compressible liquid phase (e.g. liquid water). The pressure is sufficiently low for the target fluid system to ignore the effect of mass transfer from one phase to another. In other words, the solubility of a gas into a non-compressible liquid and the vaporization of a liquid into a compressible gas can be approximated as constant without causing a significant error to the final result, as noted above.

Like the other example and as detailed below, the total volume of the high pressure side of a pumpout module is calculated, i.e., the total volume of a sample chamber and the flowline volume between sample chamber and pumpout. In addition, a supplemental volume is determined. The supplemental volume is an amount of extra volume that is pumped to over-pressurize the sample chamber after the sample chamber is substantially filled. As noted above, in some examples the supplemental volume is equal to the volume of one pump out stroke, i.e., piston stroke, and in other examples, the supplemental volume is a fraction or a multiple of the piston stroke volume. In addition, like the other example method, at the end of sample chamber filling, the example method, as noted above, includes pumping the supplemental volume to over-pressurize the sample chamber before the sample chamber is closed or isolated. The gas density is measured above the pumpout—i.e., between the pump and the sample chamber at two times: at the beginning of or before (time, $t_1$) and end of or after (time, $t_2$) the over-pressurizing supplemental volume being pumped. The two gas density readings and the known volumes are used, in accordance with the equations presented below, for example, to determine the volumes of the components of the fluid, i.e. the volumes of the non-compressible liquid (e.g., water) and the compressible gas in the sample chamber.

Turning now to the figures, FIG. 1A depicts an example wireline tool 1 in which the examples described herein can be employed. The example wireline tool 1 is suspended in a wellbore 2 from the lower end of a multiconductor cable 14 that is spooled on a winch (not shown) at the Earth's surface. At the surface, the cable 14 is communicatively coupled to an electronics and processing system 3. The example wireline tool 1 includes an elongated body 4 that includes a formation tester 20 having a selectively extendable probe assembly 22 and a selectively extendable tool anchoring member 24. In this example, the extendable probe assembly 22 and the extendable tool anchoring member 24 are arranged on opposite sides of the elongated body 4. The example formation tester may include various components including one or more receivers, transmitters, sensors and other measurement devices, etc. 5, 28, 30, 32, 36, 38.

While the wireline tool 1 is tripped out of the wellbore 2, measurements may be obtained to determine characteristics of the formation F, for example. In some examples, such measurements may be obtained by the tool 20. As described in greater detail below, the sensors, measurement devices, etc. 5, 28, 30, 32, 36, 38 may be configured to gather information about the subterranean environment and the formation fluid including parameters or characteristics such as, for example, temperature, pressure, density, composition, mobility, compressibility, etc. The gathered information may be stored in the data store 40 and may be used by the electronics and processing system 3 and/or the processing and telemetry cartridge 20 to generate a log(s) of the energy content or values detected by the sensors at different borehole depths as the wireline tool 1 is tripped out of or moved within the wellbore 2. Further examples of the gathering, manipulation, and further processing of the formation characteristics is describes below in other examples, which are implementable with the device of FIG. 1A.

Figure 1B:
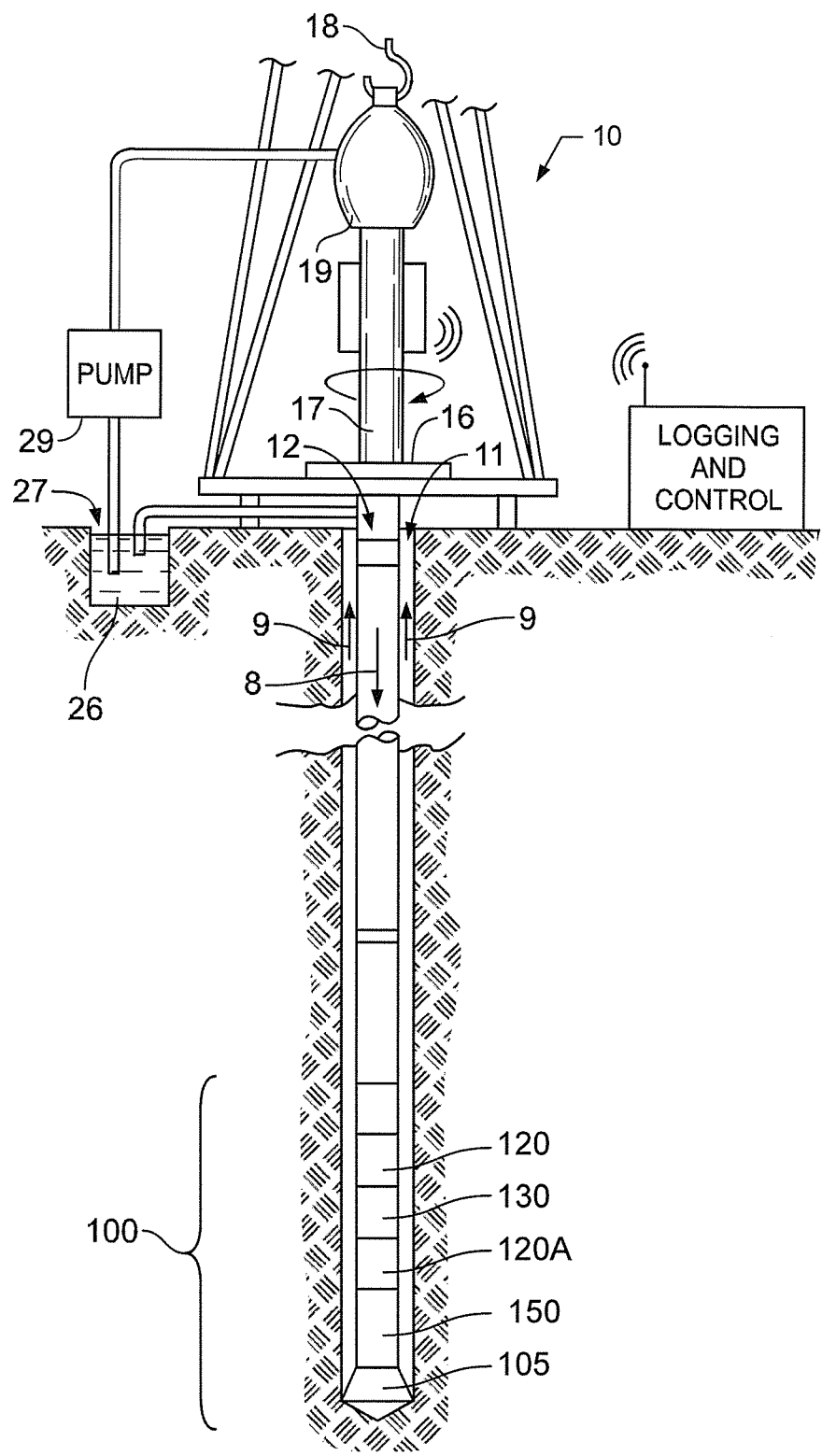
FIG. 1B illustrates an example wellsite system.

FIG. 1B illustrates an example wellsite system in which the example apparatus and method described herein can be employed. The example wellsite can be onshore or offshore. In this exemplary system, a borehole 11 is formed in subsurface formations by rotary drilling in a manner that is well known. Some examples may also use directional drilling, as will be described hereinafter.

A drill string 12 is suspended within the borehole 11 and has a bottom hole assembly 100 which includes a drill bit 105 at its lower end. The surface system includes platform and derrick assembly 10 positioned over the borehole 11, the assembly 10 including a rotary table 16, a kelly 17, a hook 18 and a rotary swivel 19. The drill string 12 is rotated by the rotary table 16, energized by means not shown, which engages the kelly 17 at the upper end of the drill string. The drill string 12 is suspended from the hook 18, attached to a traveling block (also not shown), through the kelly 17 and the rotary swivel 19, which permits rotation of the drill string 12 relative to the hook 18. As is well known, a top drive system could alternatively be used.

In this example, the surface system further includes drilling fluid or mud 26 stored in a pit 27 formed at the well site. A pump 29 delivers the drilling fluid 26 to the interior of the drill string 12 via a port in the swivel 19, causing the drilling fluid to flow downwardly through the chill string 12 as indicated by the directional arrow 8. The drilling fluid exits the drill string 12 via ports in the drill bit 105, and then circulates upwardly through the annulus region between the outside of the drill string 12 and the wall of the borehole 11, as indicated by the directional arrows 9. In this well-known manner, the drilling fluid lubricates the drill bit 105 and carries formation cuttings up to the surface as it is returned to the pit 27 for recirculation.

The bottom hole assembly 100 of the illustrated example includes a logging-while-drilling (LWD) module 120, a measuring-while-drilling (MWD) module 130, a roto-steerable system and motor 150, and the drill bit 105.

The LWD module 120 is housed in a special type of drill collar, as is known in the art, and can contain one or a plurality of known types of logging tools. It will also be understood that more than one LWD and/or MWD module can be employed, e.g. as represented at 120A. (References, throughout, to a module at the position of 120 can alternatively mean a module at the position of 120A as well.) The LWD module 120 includes capabilities for measuring, processing, and storing information, as well as for communicating with the surface equipment. In the illustrated example, the LWD module 120 includes a fluid sampling device.

The MWD module 130 is also housed in a special type of drill collar, as is known in the art, and can contain one or more devices for measuring characteristics of the drill string 12 and the drill bit 105. The MWD tool 130 further includes an apparatus (not shown) for generating electrical power to the downhole system. This may typically include a mud turbine generator powered by the flow of the drilling fluid, it being understood that other power and/or battery systems may be employed. In the illustrated example, the MWD module 130 includes one or more of the following types of measuring devices: a weight-on-bit measuring device, a torque measuring device, a vibration measuring device, a shock measuring device, a stick slip measuring device, a direction measuring device, and an inclination measuring device.

Figure 2:
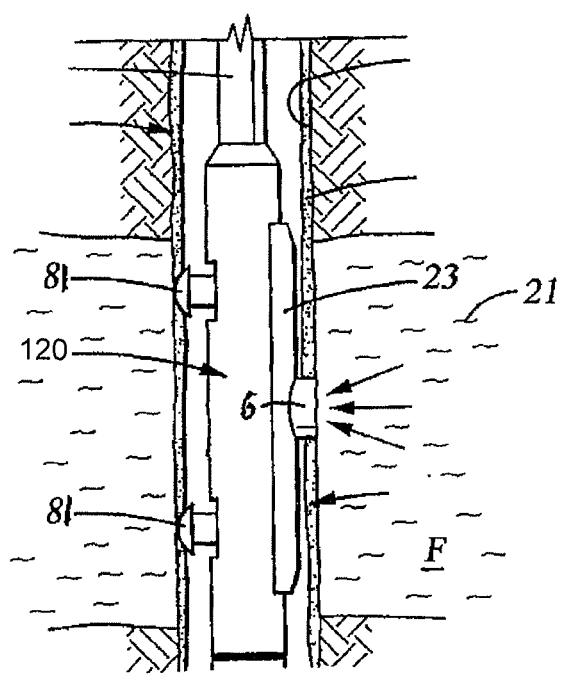
FIG. 2 illustrates a formation testing and sampling device both in wireline and logging-while-drilling.

FIG. 2 depicts an example formation testing and sampling device both in wireline and logging-while-drilling of a type described in U.S. Pat. No. 7,114,562, incorporated herein by reference in its entirety, utilized as the LWD tool 120 or part of an LWD tool suite 120A and/or as the formation testing tool 20 of the wireline device 1 of FIG. 1A. The LWD tool 120 is provided with a fluid communication device such as, for example, a probe 6 for establishing fluid communication with a formation F and drawing formation fluid 21 into the tool, as indicated by the arrows. The probe 6 may be positioned in a stabilizer blade 23 of the LWD tool 120 and extended therefrom to engage the borehole wall. The stabilizer blade 23 comprises one or more blades that are in contact with the borehole wall. Fluid drawn into the downhole tool using the probe 6 may be measured to determine, for example, pretest and/or pressure parameters. Additionally, the LWD tool 120 may be provided with devices, such as sample chambers, for collecting fluid samples for retrieval at the surface. Backup pistons 81 may also be provided to assist in applying force to push the drilling tool and/or probe against the borehole wall.

Figure 3:
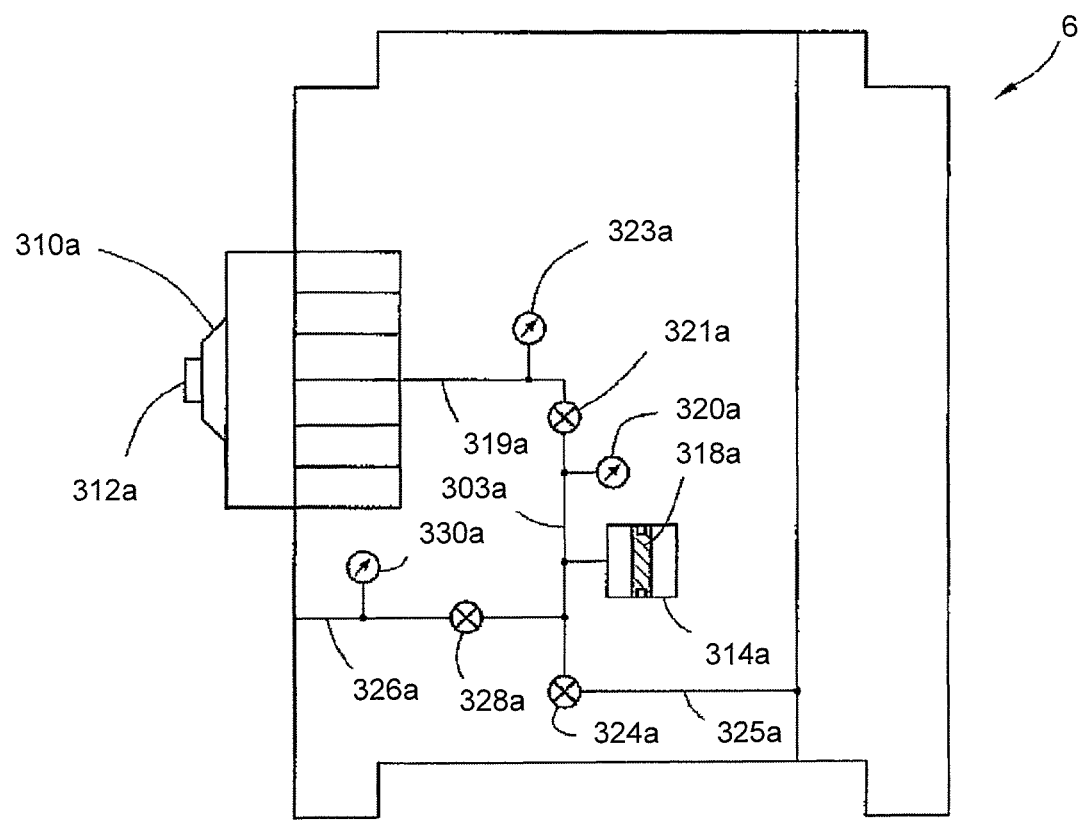
FIG. 3 illustrates an example fluid communication device.

FIG. 3 shows the example fluid communication device or probe module 6 in greater detail. The module 6 includes a probe 312a, a packer 310a surrounding the probe 312a, and a flowline 319a extending from the probe 312a into the probe module 6. The flowline 319a extends from the probe 312a to a probe isolation valve 321a, and has a pressure gauge 323a. A second flowline 303a extends from the probe isolation valve 321a to sample line isolation valve 324a and an equalization valve 328a, and has pressure gauge 320a. A reversible pretest piston 318a in a pretest chamber 314a also extends from the flowline 303a. Exit line 326a extends from the equalization valve 328a and out to the wellbore and has a pressure gauge 330a. Sample flowline 325a extends from the sample line isolation valve 324a and through the tool. Fluid sampled in the flowline 325a may be captured, flushed, or used for other purposes, as described below.

The probe isolation valve 321a isolates fluid in the flowline 319a from fluid in the flowline 303a. The sample line isolation valve 324a isolates fluid in the flowline 303a from fluid in the sample line 325a. The equalizing valve 328a isolates fluid in a wellbore from fluid in a tool. By manipulating the valves 321a, 324a and 328a to selectively isolate fluid in the flowlines, the pressure gauges 320a and 323a may be used to determine various pressures. For example, by closing the valve 321a, formation pressure may be read by the gauge 323a when the probe is in fluid communication with the formation while minimizing the tool volume connected to the formation.

In another example, with the equalizing valve 328a open, mud may be withdrawn from the wellbore into the tool by means of the pretest piston 318a. Upon closing the equalizing valve 328a, the probe isolation valve 321a and the sample line isolation valve 324a, fluid may be trapped within the tool between these valves and the pretest piston 318a. The pressure gauge 330a may be used to monitor the wellbore fluid pressure continuously throughout the operation of the tool and together with pressure gauges 320a and/or 323a may be used to measure directly the pressure drop across the mudcake and to monitor the transmission of wellbore disturbances across the mudcake for later use in correcting the measured sandface pressure for these disturbances.

Among other functions, the pretest piston 318a may be used to withdraw fluid from or inject fluid into the formation or to compress or expand fluid trapped between the probe isolation valve 321a, the sample line isolation valve 324a and the equalizing valve 328a. The pretest piston 318a preferably has the capability of being operated at low rates, for example 0.01 cm$^3$/sec, and high rates, for example 10 cm$^3$/sec, and has the capability of being able to withdraw large volumes in a single stroke, for example 100 cm$^3$. In addition, if it is necessary to extract more than 100 cm$^3$ from the formation without retracting the probe 312a, the pretest piston 318a may be recycled. The position of the pretest piston 318a can be continuously monitored and positively controlled and its position can be locked when it is at rest. In some examples, the probe 312a may further include a filter valve and a filter piston. One skilled in the art would appreciate that while the foregoing description provides one example fluid communication device or probe module configuration, other configurations may be used without departing from the scope of the disclosure.

The techniques disclosed herein may also be used with other devices incorporating a flowline. The term "flowline" as used herein shall refer to a conduit, cavity or other passage for establishing fluid communication between the formation and the pretest piston and/or for allowing fluid flow there between. Other such devices may include, for example, a device in which the probe and the pretest piston are integral. An example of such a device is disclosed in U.S. Pat. Nos. 6,230,557 and 6,986,282, assigned to the assignee of the present disclosure, both of which are hereby incorporate by reference in their entireties FIGS. 4A-E illustrate a portion of the example formation testing and sampling device both in wireline and logging-while-drilling of FIG. 2 with example valves in different open and/or closed states. As shown in FIG. 4A fluid may flow through a flowline 402, which may represent one or more of the flowlines 319a, 303a, 325a of FIG. 3, when a first valve 404 is in the open state into a pump unit 406. A second valve 408 is in the closed state in FIG. 4A to cause the fluid to collect in the pump unit 406. When fluid has collected in the pump unit 406, as shown in FIG. 4B, the first valve 404 moves to a closed position. In this example, the fluid collected in the pump unit 406 may substantially fill the pump unit 406.

Figure 4C:
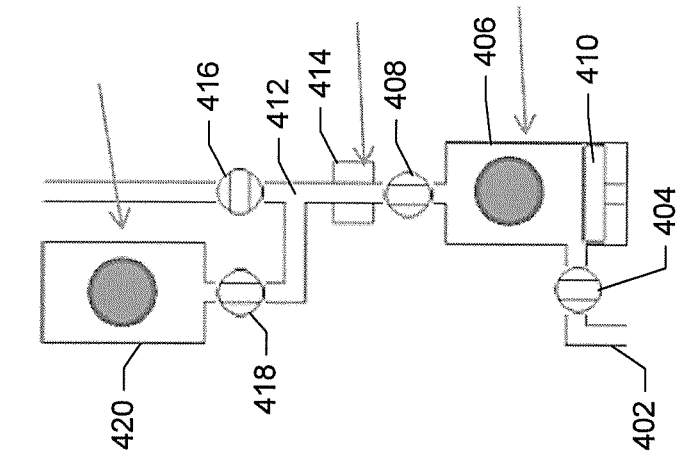
FIGS. 4A-E illustrate a portion of the example formation testing and sampling device both in wireline and logging-while-drilling of FIG. 2 with example valves in different open/closed states.
Figure 4B:
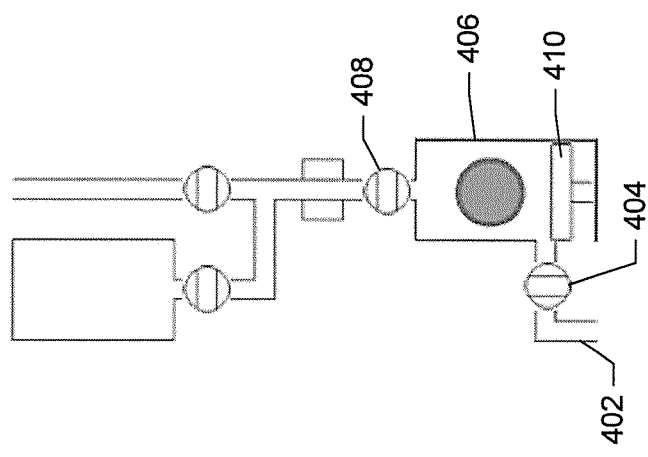
Figure 4A:
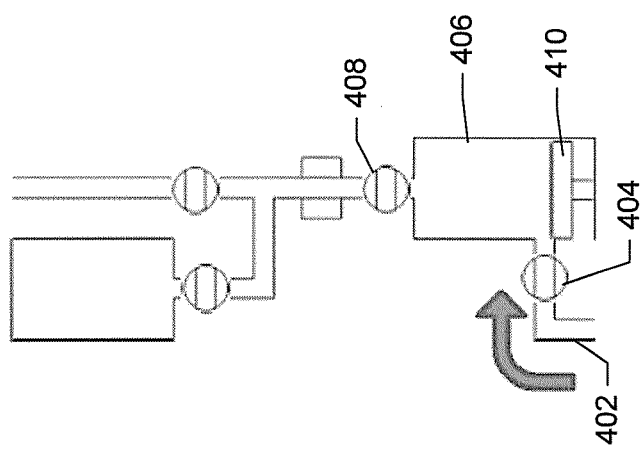
Figure 4E:
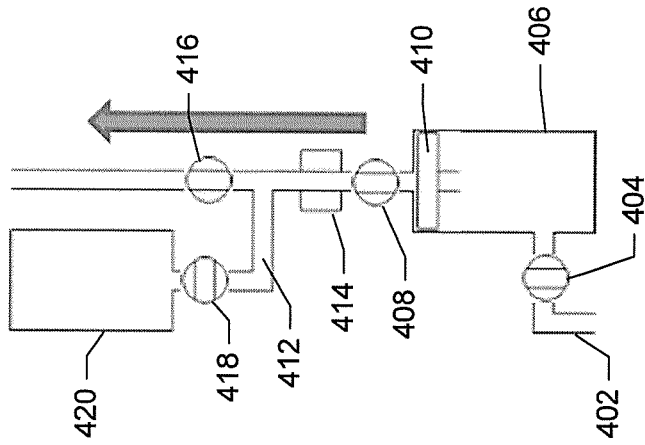
Figure 4D:
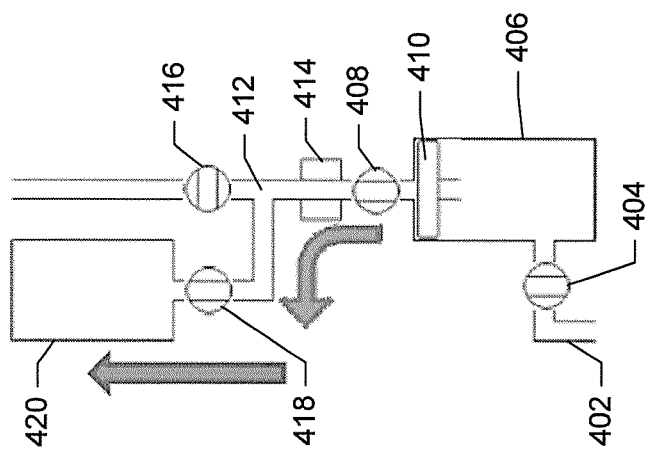

FIG. 4C shows the second valve 408 in the open position, which enables the fluid to flow from the pump unit 406 for example, when a piston 410 in the pump unit 406 moves from the back position (FIG. 4C) to the front position (FIG. 4D). As the piston 410 moves from the back position to the front position, the piston 410 expels the fluid content of the pump unit 406 into a second flowline 412 and past a downhole fluid analyzer (DFA) module 414. The DFA module 414 contains one or more sensors to measure characteristics of the fluid including, for example, temperature, pressure, velocity, density, composition, etc. A third valve 416 in the flowline is in the closed position and a fourth valve 418 is in the open position to cause the fluid to flow toward and into a sample chamber 420.

FIG. 4E illustrates another configuration in which the third valve 416 is in the open position and the fourth valve 418 is in the closed position. In this example, the fluid flows to another portion of the tool or out of the tool. In the examples of FIGS. 4A-4E, the valves 404, 408, 416, 418, flowlines 402, 404 and piston 410 may be identical or similar to the valves 321a, 324a, 328a, flowlines 319a, 303a, 325a and piston 318a described with respect to FIG. 3.

Figure 5:
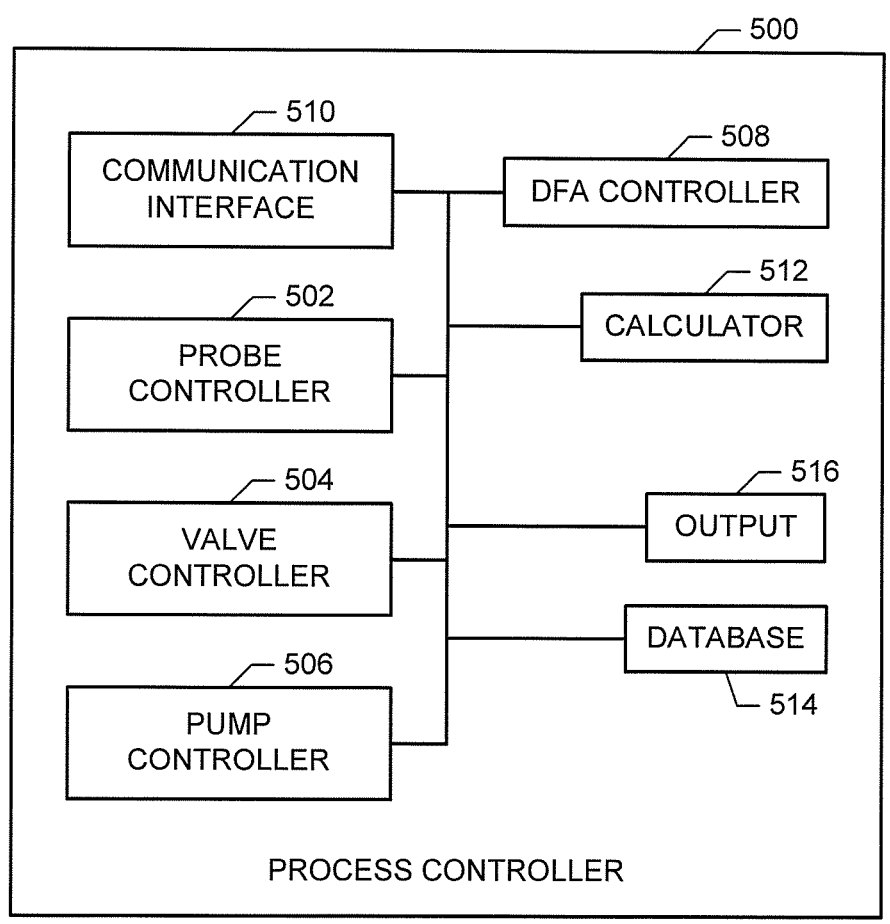
FIG. 5 is a schematic representation of an example process controller that is communicatively coupled to the example formation testing and sampling device both in wireline and logging-while-drilling.

FIG. 5 is a schematic depiction of an example process controller 500 that may be used to operate the apparatus of FIGS. 1-3 and 4A-4E. The example process controller 500 includes a probe controller 502 to manage operation of the probe assembly 6 and/or the probe 312a. The example process controller 500 also includes a valve controller 504 to manage the valves 321a, 324a, 328s, 404, 408, 410 and/or 418. The example process controller 500 also includes a pump controller 506 to manage operation of the piston 319 and/or 410. In addition, the example controller 500 includes a DFA controller 508 to manage operation of the DFA module 414. The example process controller 500 communicates with the components of the example apparatus described herein via a communications interface 510. The communications interface 510 may communicate commands and/or information via wired or wireless communications networks.

In operation, the process controller 500 uses the probe controller 502 to instruct the probe 312a to extend to the wall of the borehole 11 to create a fluid communication with the formation or reservoir 21. The process control 500 may use the valve controller 504 to instruct the first valve 402 to move to the open position and the second valve 408 to move to the closed position while the piston 410 is instructed, via the probe controller 506, to move to the back position as shown in FIG. 4A to allow fluid to flow into the pump unit 406. Then, the process controller 500 instructs, via the valve controller 504, the first valve 402 to close and the second valve 408 to open. The pump controller 506 is used by the process controller 500 to instruct the piston 410 to produce one or more strokes to expel the fluid from the pump unit 406 (FIGS. 4B-D). With the valve controller 504 being used to instruct the third valve 416 to close and the fourth valve 418 to open, the fluid flows from the pump unit 406 into the sample bottle or chamber 420.

When the DFA module 414 and/or other sensor(s) senses that the sample chamber 420 is full or substantially full, the process controller 500 repeats the sequence of opening and closing the various valves 404, 408, 416 and/or 418 and instructs the piston 410 to provide at least one additional stroke to over-pressurize the fluid in the sample chamber 420.

The example process controller 500 also includes a calculator 512 and a memory or database 514. The DFA module 414, the calculator 512 and/or other sensors (e.g., the pressure gauges 323a and 330a of FIG. 3 and/or the InSitu density sensor of Schlumberger) measure various characteristics of the fluid and elements of the example tool. For example, one or more of these components may measure or otherwise determine a temperature, a pressure, a density, a composition, a velocity and/or a volume or any other characteristic of the fluid or elements of the tool. In some examples, the DFA module 414, DFA controller 508 and/or the calculator are provided with or measure a volume of the sample chamber 420, a volume of the flowline between the output end of the pump unit 406 and the input of the sample chamber 420 and a volume of one stroke of the piston 410. In some examples, these volumes may be provided prior to performing the methods and processes described herein. As fluid flows past the DFA module 414, the DFA module 414, the DFA controller 508 and/or the calculator measure or determine characteristics of the passing fluid including the temperature, pressure, composition and density. Once the process controller 500 senses that the sample chamber 420 is full or substantially full, as noted above, the DFA module 414, the DFA controller 508 and/or the calculator 512 record the temperature, pressure and/or gas density of the fluid at that time. The recorded figures may be stored in the database 514. After the piston 410 provides the at least one further stroke to over-pressurize the sample chamber 420, the DFA module 414, the DFA controller 508 and/or the calculator 512 record the temperature, pressure, composition and/or gas density of the fluid at that subsequent time. These recorded figures also may be stored in the database 514.

In one example operation, the calculator 512 may use the pressure and temperature data to determine or estimate fluid component volumes. That is, the pressure and temperature data may be used to determine what fraction or percentage of the volume of the fluid is in the gas phase and what fraction or percentage of the volume of the fluid is in the liquid phase. To facilitate this determination, the calculator 512 may perform calculations based on the basic equation of state, PV=nRT, and/or any other equation of state. For example, the calculator 512 may perform calculations based on Equations 1 and 2 below.

$$P_1(X+Y-Z)=nRT_1, \quad (1)$$

$$P_2(X-Z)=nRT_2, \quad (2)$$

Where $P_1$, $(X+Y-Z)$ and $T_1$ represent the pressure, volume occupied by gas and temperature, respectively, at a first time, i.e., when the sample chamber is filled or substantially filled. Similarly, $P_2$, $(X-Z)$ and $T_2$ represent the pressure, volume occupied by gas and temperature, respectively, at a second time, i.e., after the supplemental volume is added when the sample chamber is over-pressurized. The variable X corresponds to the total volume of the high pressure side of the pump unit 406, i.e., the total volume of the sample chamber 420 and the flowline 412 between the sample chamber 420 and the pump unit 406. The variable Y corresponds to the total volume of the supplemental volume used to over-pressurize the sample chamber which may be, in one example, the volume of one piston stroke or a fraction or multiple of the volume of one piston stroke. The variable Z corresponds to the total volume of fluid in the liquid phase, i.e., the non-compressible fluid, and n remains constant as it is a total amount of gas molecules. As noted above, the pressure is sufficiently low for the target fluid system to ignore the effect of mass transfer from one phase to another and, thus, the example calculator 512, for example, can estimate the solubility of the gas phase into the non-compressible liquid phase and the vaporization of the liquid phase into the compressible gas phase as constant.

Z corresponds to the component volume of the fluid that is a substantially non-compressible liquid, and X–Z corresponds to the total component volume of the fluid that is a compressible gas.

In another example operation, the calculator 512 may use the gas density data to determine or estimate fluid component volumes. That is, the gas density data may be used to determine what fraction or percentage of the volume of the fluid is in the gas phase and what fraction or percentage of the volume of the fluid is in the liquid phase. To facilitate this determination, the calculator 512 may perform calculations based on Equation 3 below.

$$D_1(X+Y-Z)=D_2(X-Z) \tag{11}$$

Where $D_1$ represents the gas density at the first time, i.e., when the sample chamber is substantially filled, and $D_2$ represents the gas density data at the second time, i.e., after the supplemental volume is added when the sample chamber is over-pressurized. The variable X corresponds to the total volume of the high pressure side of the pump unit 406, i.e., the total volume of the sample chamber 420 and the flowline 412 between the sample chamber 420 and the pump unit 402. The variable Y corresponds to the total volume of the supplemental volume that is used to over-pressurize the chamber, e.g., one piston stroke. The variable Z corresponds to the total volume of fluid in the liquid phase, i.e., the non-compressible fluid, as mentioned above.

Equation 3 is solved for Z, as shown below in Equations 4-7:

$$D_1X+D_1Y-D_1Z=D_2X-D_2Z \tag{4}$$

$$D_2Z-D_1Z=D_2X-D_1X-D_1Y \tag{5}$$

$$Z(D_2-D_1)=D_2X-D_1X-D_1Y \tag{6}$$

$$Z=(D_2X-D_1X-D_1Y)/(D_2-D_1) \tag{7}$$

Where Z is the component volume of the fluid that is a substantially non-compressible liquid, and X–Z is the total component volume of the fluid that is a compressible gas.

Once the component volume of the fluid that is a substantially non-compressible liquid and the total component volume of the fluid that is a compressible gas are determined, the results may be stored in the database 514 and/or output to an operator of the tool via an output 516, which may be, for example, a display.

The example database 514 stores known properties of the tool (e.g., the non-variable volumes noted above). The database 514 may also store the variable data and the estimations of the fluid component volumes of the sampled fluid. The data within the database 514 may be updated, added to, deleted, and/or modified by an operator such as, for example, via the communications interface 510. For example, an operator may modify the volume of a piston stroke after a redesign or reconfiguration of the tool. The database 514 may be implemented by random access memory (RAM), read-only memory (ROM), a programmable ROM (PROM), an electronically-programmable ROM (EPROM), an electronically-erasable PROM (EEPROM), and/or any other type of memory.

While an example manner of implementing the process controller 500 is depicted in FIG. 5, one or more of the interfaces, data structures, elements, processes and/or devices illustrated in FIG. 5 may be combined, divided, rearranged, omitted, eliminated and/or implemented in any other way. For example, the example probe controller 502, valve controller 504 and pump controller 506 may be implemented separately and/or in any combination using, for example, machine-accessible or readable instructions executed by one or more computing devices and/or computing platforms (e.g., the example computing system 7 of FIG. 7). In addition, the calculator 512 may be combined with the example DFA controller 508 in a similar manner.

Further, the communications interface 510, the probe controller 502, the valve controller 504, the pump controller 506, the DFA controller 508, the calculator 512 and/or, more generally, the example process controller 500 may be implemented by hardware, software, firmware and/or any combination of hardware, software and/or firmware. Thus, for example, any of the communications interface 510, the probe controller 502, the valve controller 504, the pump controller 506, the DFA controller 508, the calculator 512 and/or, more generally, the example process controller 500 can be implemented by one or more circuit(s), programmable processor(s), application specific integrated circuit(s) (ASIC(s)), programmable logic device(s) (PLD(s)) and/or field programmable logic device(s) (FPLD(s)), etc.

Figure 6:
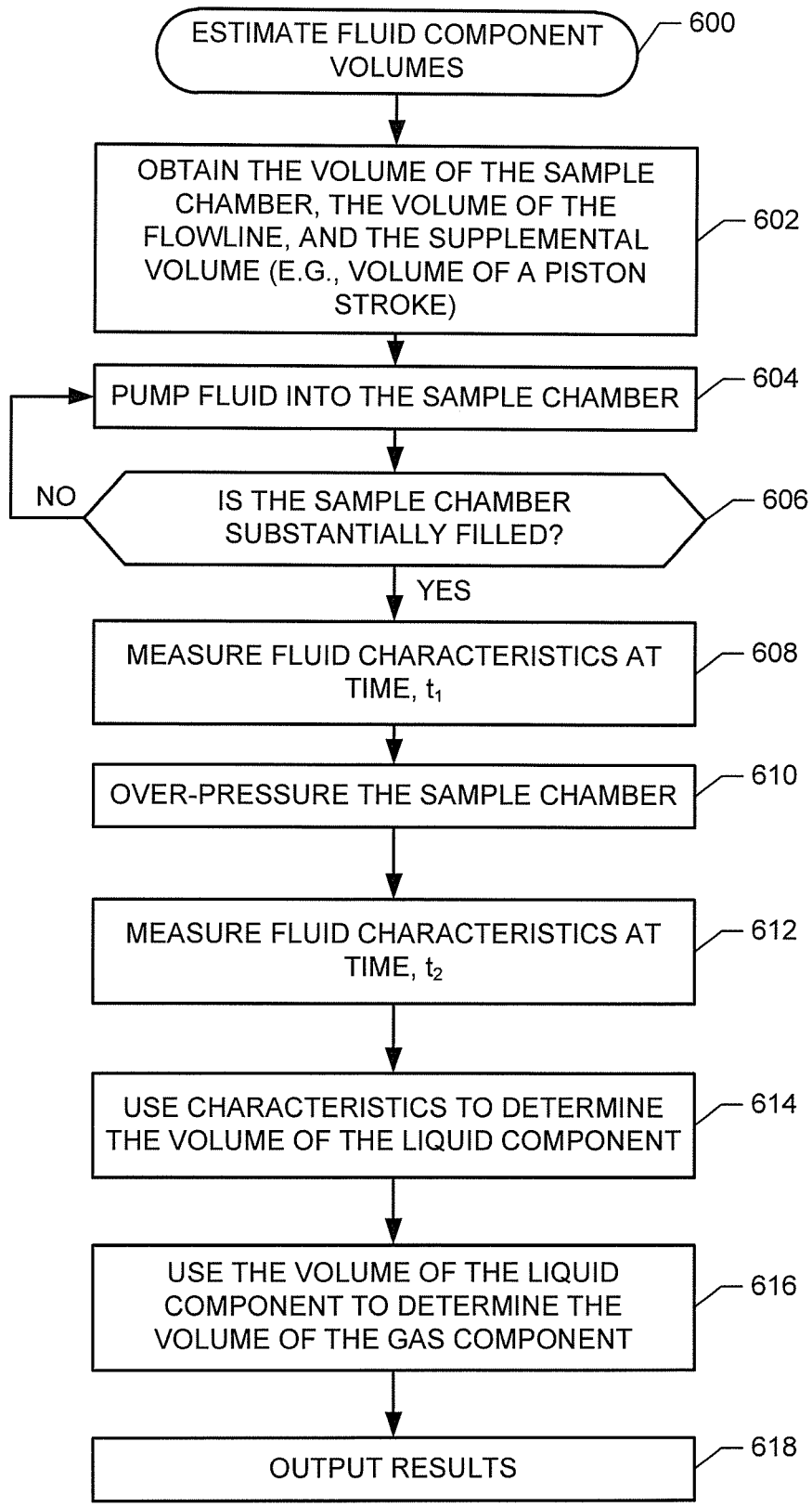
FIG. 6 is a flow chart showing an example method for estimating fluid component volumes.

FIG. 6 is a flowchart depicting an example process 600 that may be carried out to implement the process controller 500, the communications interface 510, the probe controller 502, the valve controller 504, the pump controller 506, the DFA controller 508, the calculator 512, the DFA module 414, the valves 321a, 324a, 328a, 404, 408, 416, 418, the pump unit 406, the pistons 318a, 410 and the pressure gauges 323a, 330a of FIGS. 3, 4A-4E and 5. The example process of FIG. 6 may be carried out by a processor, a controller and/or any other suitable processing device. For example, the example process of FIG. 6 may be embodied in coded instructions stored on any tangible computer-readable medium such as a flash memory, a CD, a DVD, a floppy disk, a ROM, a RAM, a programmable ROM (PROM), an electronically-programmable ROM (EPROM), an electronically-erasable PROM (EEPROM), an optical storage disk, an optical storage device, magnetic storage disk, a magnetic storage device, and/or any other medium that can be used to carry or store program code and/or instructions in the form of methods, processes or data structures, and which can be accessed by a processor, a general-purpose or special-purpose computer, or other machine with a processor (e.g., the example computing system 700 discussed below in connection with FIG. 7). Combinations of the above are also included within the scope of computer-readable media.

Processes comprise, for example, instructions and/or data that cause a processor, a general-purpose computer, special-purpose computer, or a special-purpose processing machine to implement one or more particular processes or operations. Alternatively, some or all of the example operations of FIG. 6 may be implemented using any combination(s) of ASIC(s), PLD(s), FPLD(s), discreet logic, hardware, firmware, etc.

Also, one or more of the example operations of FIG. 6 may be implemented using manual operations or as any combination of any of the foregoing techniques, for example, any combination of firmware, software, discreet logic and/or hardware. Further, other processes implementing the example operations of FIG. 6 may be employed. For example, the order of execution of the blocks or operations may be changed, and/or one or more of the blocks described may be changed, eliminated, sub-divided, or combined. Additionally, any or all the example operations of FIG. 6 may be carried out sequentially and/or carried out in parallel by, for example, separate processing threads, processors, devices, discreet logic, circuits, etc.

The example process 600 of FIG. 6 analyzes a sampled fluid in a downhole tool to estimate or determine the fluid component volumes such as, for example, the volume of the component of the fluid that is a substantially non-compressible liquid and the volume of the component of the fluid that is a compressible gas. The example process 600 obtains the volume of a sample chamber, the volume of a flowline and the supplemental volume (block 602) by, for example, using the example process controller 500 of FIG. 5 to read these volume measurements from sensors arranged in the tool and/or from recorded data stored in the example database 514, which, for example, may have been recorded prior to utilization of the apparatus described herein or implementation of the related methods. The supplemental volume is the volume used in over-pressurizing the sample chamber, which may be, as noted above, the volume of a piston stroke. In other examples, the supplemental volume may be a fraction or a multiple of the volume of the piston stroke, as noted above.

The example process 600 pumps fluid into the sample chamber (block 604), by for example, controlling the valves 404, 408, 416 and 418 with the example valve controller 504 and the piston 410 with the example pump controller 506 as detailed above. The example process then determines if the sample chamber is substantially filled (block 606). The determination may be made by the DFA module 414, the DFA controller 508, the calculator 512 and/or any other sensor(s). If the sample chamber 420 is not substantially filled, the pump unit 406 continues to pump fluid into the sample chamber 420 (block 604). Once it is determined that the sample chamber 420 is substantially filled (block 606), the example process 600 measures characteristics of a fluid sample at a first time, $t_1$ (block 608). In this example, the fluid characteristics are measured by, for example, the DFA module 414. The characteristics may be any type of fluid characteristic including, for example, a pressure, a temperature and/or a gas density. Also, the time, $t_1$ occurs after the piston stroke that leaves the sample chamber 420 substantially filled.

Once the measurements of the fluid characteristics at the first time are taken and/or recorded in the database 512, the example process 600 over-pressurizes the sample chamber (block 610) with the addition of supplemental volume. In one example, the supplemental volume use to over-pressurize the sample chamber 420 is the volume of one more stroke of the piston 410 after the sample chamber is substantially filled. In other examples, the volume of any number of extra strokes or fractions of extra strokes may be used as the supplemental volume to over-pressurize the sample chamber 420. After the over-pressurization of the sample chamber 420, the process 600 includes measuring the fluid characteristics (e.g., pressure, temperature and/or gas density) at a second time, $t_2$ (block 612). The characteristics may be measured a second time by, for example, the DFA module 414. The time, $t_2$ occurs after the addition of the supplemental volume that leaves the sample chamber 420 substantially filled.

Once the characteristics have been measure before (block 608) and after (block 612) the over-pressurization of the sample chamber 420, the characteristics can be used to determine the volume of the liquid component (block 614). For example, the calculator 512 may use pressure and temperature characteristics and determine the volume fraction or percentage of the liquid phase component (e.g., the substantially non-compressible liquid portion) of the sampled fluid by using Equations 1-3, detailed above. The liquid component is represented by the variable Z. In an alternative example, the calculator 512 may use gas density characteristics and determine the volume fraction or percentage of the liquid phase component of the sampled fluid by using Equations 4-7, detailed above. The liquid component is again represented by the variable Z.

With the volume fraction or percentage of the liquid phase component known, the volume of the gas component (e.g., a compressible gas) is determined (block 616). For example, as detailed above, the calculator 512 may subtract the volume fraction or percentage of the liquid phase component from the sum of the volume of the volume of the sample chamber 420 and the volume of the flowline 412 between the pump unit 406 and the sample chamber 420. The results of the determination/estimation of the fluid component volumes may be output (block 618) to, for example, an operator via the example output 516.

Figure 7:
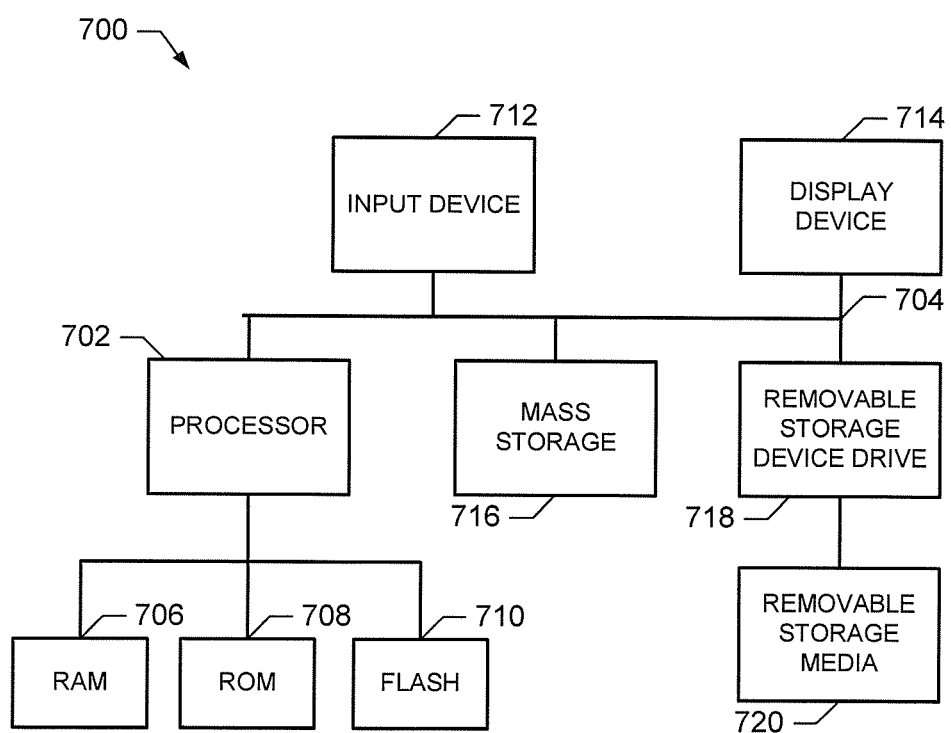
FIG. 7 is a block diagram of an example processor system that may be used to implement the example methods and apparatus described herein.

FIG. 7 is a block diagram of an example computing system 700 that may be used to implement the example methods and apparatus described herein. For example, the computing system 700 may be used to implement the example process controller 500, the example communications interface 502, the example probe controller 502, the example valve controller 504, the example pump controller 506, the example DFA controller 508, the example DFA module 414, the example calculator 512 and/or the example output 516. The example computing system 700 may be, for example, a conventional desktop personal computer, a notebook computer, a workstation or any other computing device. A processor 702 may be any type of processing unit, such as a microprocessor from the Intel® Pentium® family of microprocessors, the Intel® Itanium® family of microprocessors, the Intel® Core™ family of microprocessors, and/or the Intel XScale® family of processors. Memories 706, 708 and 710 that are coupled to the processor 702 may be any suitable memory devices and may be sized to fit the storage demands of the system 700. In particular, the flash memory 710 may be a non-volatile memory that is accessed and erased on a block-by-block basis.

An input device 712 may be implemented using a keyboard, a mouse, a touch screen, a track pad or any other device that enables a user to provide information to the processor 1902.

A display device 714 may be, for example, a liquid crystal display (LCD) monitor, a cathode ray tube (CRT) monitor or any other suitable device that acts as an interface between the processor 702 and a user. The display device 714 as pictured in FIG. 7 includes any additional hardware required to interface a display screen to the processor 702.

A mass storage device 716 may be, for example, a conventional hard drive or any other magnetic or optical media that is readable by the processor 702.

A removable storage device drive 718 may, for example, be an optical drive, such as a compact disk-recordable (CD-R) drive, a compact disk-rewritable (CD-RW) drive, a digital versatile disk (DVD) drive or any other optical drive. It may alternatively be, for example, a magnetic media drive. A removable storage media 720 is complimentary to the removable storage device drive 718, inasmuch as the media 720 is selected to operate with the drive 718. For example, if the removable storage device drive 718 is an optical drive, the removable storage media 720 may be a CD-R disk, a CD-RW disk, a DVD disk or any other suitable optical disk. On the other hand, if the removable storage device drive 718 is a magnetic media device, the removable storage media 720 may be, for example, a diskette or any other suitable magnetic storage media.

At least some of the above described example methods and/or apparatus are implemented by one or more software and/or firmware programs running on a computer processor.

However, dedicated hardware implementations including, but not limited to, application specific integrated circuits, programmable logic arrays and other hardware devices can likewise be constructed to implement some or all of the example methods and/or apparatus described herein, either in whole or in part. Furthermore, alternative software implementations including, but not limited to, distributed processing or component/object distributed processing, parallel processing, or virtual machine processing can also be constructed to implement the example methods and/or systems described herein.

It should also be noted that the example software and/or firmware implementations described herein are stored on a tangible storage medium, such as: a magnetic medium (e.g., a magnetic disk or tape); a magneto-optical or optical medium such as an optical disk; or a solid state medium such as a memory card or other package that houses one or more read-only (non-volatile) memories, random access memories, or other re-writable (volatile) memories. Accordingly, the example software and/or firmware described herein can be stored on a tangible storage medium such as those described above or successor storage media.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. §1.72(b) to allow the reader to quickly ascertain the nature of the technical disclosure. It is submitted with the understanding that it will not be used to interpret or limit the scope or meaning of the claims.

What is claimed is:

1. A method of estimating one or more volumes of one or more components of a fluid in a sample chamber of a downhole tool, the method comprising:
    obtaining a sample chamber volume measurement;
    obtaining a flowline volume measurement;
    obtaining a supplemental volume measurement;
    drawing the fluid into the sample chamber until the sample chamber is substantially full;
    measuring a characteristic of the fluid in the sample chamber at a first time to obtain a first characteristic measurement;
    adding a supplemental volume corresponding to the supplemental volume measurement to over-pressurize the sample chamber after measuring the characteristic at the first time;
    measuring the characteristic of the fluid in the sample chamber at a second time to obtain a second characteristic measurement, the second time being after the sample chamber is over-pressurized; and
    calculating a first volume of a first component of the one or more components of the fluid based on the first characteristic measurement, the second characteristic measurement, the sample chamber volume measurement, the flowline volume measurement and the supplemental volume measurement.

2. A method as defined in claim 1 wherein the characteristic is a pressure and a temperature.

3. A method as defined in claim 1 wherein the characteristic is a density.

4. A method as defined in claim 1 wherein the first component of the fluid is in a liquid phase and a second component of the fluid is in a gas phase and further comprising estimating a constant for the solubility of the second component in the first component and the vaporization of the first component in the second component.

5. A method as defined in claim 1 wherein the supplemental volume measurement is substantially equal to a volume of one piston stroke.

6. A method as defined in claim 1 wherein the first component has a first velocity and a second component has a second velocity different than the first velocity.

7. A method as defined in claim 1 further comprising subtracting the first volume of the first component from the sum of the flowline volume measurement and the sample chamber volume measurement to determine a second volume of a second component of the one or more components of the fluid.

8. A method as defined in claim 7 wherein the first component is a substantially non-compressible liquid and the second component is a compressible gas.

9. A tangible machine readable medium having instructions stored thereon which, when executed, cause a machine to estimate one or more volumes of one or more components of a fluid in a sample chamber of a downhole tool by causing the machine to:
    obtain a sample chamber volume measurement;
    obtain a flowline volume measurement;
    obtain a supplemental volume measurement; and
    draw the fluid into the sample chamber until the chamber is substantially full;
    measure a characteristic of the fluid in the sample chamber at a first time to obtain a first characteristic measurement;
    add a supplemental volume corresponding to the supplemental volume measurement to over-pressurize the sample chamber after the measuring of the characteristic of the fluid at the first time;
    measure the characteristic of the fluid in the sample chamber at a second time to obtain a second characteristic measurement, the second time being after the sample chamber is over-pressurized; and
    calculate a first volume of a first component of the one or more components of the fluid based on the first characteristic measurement, the second characteristic measurement, the sample chamber volume measurement, the flowline volume measurement and the supplemental volume measurement.

10. A machine readable medium as defined in claim 9 wherein the characteristic of the fluid is at least one of a pressure or a temperature.

11. A machine readable medium as defined in claim 9 wherein the characteristic of the fluid is a density.

12. A machine readable medium as defined in claim 9 wherein the first component of the fluid is in a liquid phase and a second component of the fluid is in a gas phase and when the instructions are executed the machine is caused to estimate a constant for the solubility of the second component in the first component and the vaporization of the first component in the second component.

13. A machine readable medium as defined in claim 9 wherein the supplemental volume measurement is substantially equal to a volume of one piston stroke.

14. A machine readable medium as defined in claim 9 wherein the first component has a first velocity and a second component has a second velocity different than the first velocity.

15. A machine readable medium as defined in claim 9 which, when executed, causes the machine to subtract the first volume of the first component from the sum of the flowline volume measurement and the sample chamber volume measurement to determine a second volume of a second component of the one or more components of the fluid.

16. A machine readable medium as defined in claim 15 wherein the first component is a substantially non-compressible liquid and the second component is a compressible gas.

17. A downhole tool comprising:
   a sample chamber having a sample chamber volume;
   a flowline coupled to the sample chamber and having a flowline volume;
   a pump to pump a fluid into the sample chamber through the flowline,
   a sensor to measure a characteristic of the fluid in the sample chamber when the sample chamber is substantially full at a first time to obtain a first characteristic measurement and to measure the characteristic of the fluid in the sample chamber at a second time to obtain a second characteristic measurement, the first time being before the pump over-pressurizes the sample chamber and the second time being after the pump pumps a supplemental volume into the sample chamber to overpressurize the sample chamber; and
   a calculator to determine a first volume of a first component of the one or more components of the fluid based on the first characteristic measurement, the second characteristic measurement, the sample chamber volume, the flowline volume and the supplemental volume.

18. A downhole tool as defined in claim 17 wherein the characteristic of the fluid is at least one of a pressure or a temperature.

19. A downhole tool as defined in claim 17 the characteristic of the fluid is a density.

20. A downhole tool as defined in claim 17 wherein the first component of the fluid is in a liquid phase and a second component of the fluid is in a gas phase and the calculator is to estimate a constant for the solubility of the second component in the first component and the vaporization of the first component in the second component.

21. A downhole tool as defined in claim 17 wherein the supplemental volume is substantially equal to a volume of one piston stroke of the pump.

22. A downhole tool as defined in claim 17 wherein the first component has a first velocity and a second component has a second velocity different than the first velocity.

23. A downhole tool as defined in claim 17 wherein the calculator is to subtract the first volume of the first component from the sum of the flowline volume and the sample chamber volume to determine a second volume of a second component of the one or more components of the fluid.

24. A downhole tool as defined in claim 23 wherein the first component is a substantially non-compressible liquid and the second component is a compressible gas.

25. A method of estimating one or more component volumes of one or more components of a sample fluid in a downhole tool, the method comprising:
   obtaining a volume of the sample fluid contained in the downhole tool;
   measuring a characteristic of the sample fluid at a first time to obtain a first characteristic measurement;
   pumping a supplemental volume to overpressurize the sample fluid;
   measuring the characteristic of the sample fluid a second time to obtain a second characteristic measurement; and
   calculating a first component volume of a first component of the one or more components of the sample fluid based on at least the first characteristic measurement, the second characteristic measurement, the volume, and the pumped supplemental volume.

26. A downhole tool as described in claim 25, wherein the volume of the sample fluid includes at least one of a sample chamber volume measurement, a flowline volume measurement, or a supplemental volume measurement.

27. A downhole tool as described in claim 25, wherein the volume of the sample fluid includes at least a sample chamber volume measurement, a flowline volume measurement, and a supplemental volume measurement.

28. A non-transitory machine readable medium having instructions stored thereon which, when executed, cause a machine to estimate one or more volumes of one or more components of a sample fluid in a downhole tool by causing the machine to:
   obtain a volume of the sample fluid in the downhole tool;
   measure a characteristic of the sample fluid in at a first time to obtain a first characteristic measurement;
   pumping a supplemental volume to overpressurize the sample fluid;
   measure the characteristic of the sample fluid at a second time to obtain a second characteristic measurement; and
   calculate a first volume of a first component of the one or more components of the fluid based on the first characteristic measurement, the second characteristic measurement, the volume, and the pumped supplemental volume.

29. A machine as described in claim 28, wherein the volume of the sample fluid includes at least one of a sample chamber volume measurement, a flowline volume measurement, or a supplemental volume measurement.

30. A machine as described in claim 28, wherein the volume of the sample fluid includes at least a sample chamber volume measurement, a flowline volume measurement, and a supplemental volume measurement.

* * * * *